United States Patent [19]
Defaye et al.

[11] Patent Number: 6,080,733
[45] Date of Patent: Jun. 27, 2000

[54] THIOUREIDO-CYCLODEXTRINS, UTILIZED IN PARTICULAR TO SOLUBILIZE ANTI-TUMOR, AND ANTIPARASITIC AGENTS AND THEIR PREPARATION PROCESSES

[75] Inventors: Jacques Defaye, Saint Ismier, France; Carmen Ortiz-Mellet; José-Manuel Garcia-Fernandez, both of Seville, Spain

[73] Assignee: Centre National de la Recherche Scientifique, Paris, France

[21] Appl. No.: 09/147,023

[22] PCT Filed: Mar. 13, 1997

[86] PCT No.: PCT/FR97/00449

§ 371 Date: Oct. 20, 1998

§ 102(e) Date: Oct. 20, 1998

[87] PCT Pub. No.: WO97/33919

PCT Pub. Date: Sep. 18, 1997

[30] Foreign Application Priority Data

Mar. 14, 1996 [FR] France ................................ 96 03221

[51] Int. Cl.$^7$ .................................................. A01N 43/04
[52] U.S. Cl. .............................. 514/58; 424/10; 536/103; 549/510; 549/511
[58] Field of Search .............................. 514/58; 549/510, 549/511; 424/10; 536/103

[56] References Cited

U.S. PATENT DOCUMENTS 5,684,169  11/1997  Hamada et al. ...................... 549/510

FOREIGN PATENT DOCUMENTS 0 403 366  12/1990  European Pat. Off. .
0 605 753  7/1994  European Pat. Off. .
WO 95/21870  8/1995  WIPO .

OTHER PUBLICATIONS

P. Potier, Chem. Soc. Rev., vol. 21, pp. 113–119, "Search and Discovery of New Antitumour Compounds", 1992.

M.C. Bissery, et al. Cancer Research, vol. 51, pp. 4845–4852, "Experimental Antitumor Activity of Taxotere (RP56976, NSC 628503), A Taxol Analogue", Sep. 15, 1991.

V. Lainé, et al., J. Chem. Soc., Perkin Trans., vol. 2, pp. 1479–1487, "Inclusion and Solubilization Properties of 6–S–Glycosal–6–Thio Derivatives of β–Cyclodextrin", 1995.

J. Schrével, et al., Proc. Nat. Acad. Sci. USA, vol. 91, pp. 8472–8476, "Interactions Between Docetaxel (Taxotere) and *Plasmodium Falciparum*–Infected Erythrocytes", Aug., 1994.

C.M. Reichert, et al., Methods in Enzymology, vol. 242, pp. 108–116, "Coupling of Carbohydrates to Proteins by Diazonium and Phenylisothiocyanate Reactions", 1994.

J.M. Garcia Fernandez, et al., Carbohydrate Research, vol. 268, pp. 57–71, "Isothiocyanates and Cyclic Thiocarbamates of αα'–Trehalose, Sucrose, and Cyclomaltooligosaccharides", 1995.

R.C. Petter, et al., J. Am. Chem. Soc., vol. 112, pp. 3860–3868, "Cooperative Binding by Aggregated Mono–6–(Alkylamino)–β–Cyclodextrins", 1990.

S.E. Brown, et al., Aust. J. Chem., vol. 46, pp. 953–958, "Synthesis and Properties of $6^A$–Amino–$6^A$–Deoxy–α–and–β–Cyclodextrin", 1993.

J.M. Garcia Fernandez, et al. J. Org. Chem., vol. 58, pp. 5192–5199, "Chiral 2–Thioxotetrahydro–1,3–O, N–Heterocycles from Carbohydrates. 2. Stereocontrolled Synthesis of Oxazolidine Pseudo–C–Nucleosides and Bicyclic Oxazine–2–Thiones", 1993.

K. Dax, et al., J. Carbohydrate Chemistry, vol. 9, No. 4, pp. 479–499, "Easy Synthesis of 1,5–Didesoxy–1,5–Imino–o–d–Glycitol (1–Desoxynozirimycin) and 1,6–Didesoxy–1, 6–Dimino–D–Glucitol from D–Glucofuranurono–6,3–Lactone", (With English Abstract), 1990.

Z.J. Witczak, Advances in Carbohydrate Chemistry and Biochemistry, vol. 44, pp. 91–145, "Monosaccharide Isothiocyanates and Thiocyanates: Synthesis, Chemistry, and Preparative Applications", 1986.

*Primary Examiner*—James O. Wilson
*Attorney, Agent, or Firm*—Oblon, Spivak, McClelland, Maier & Neustadt, P.C.

[57] ABSTRACT

The invention relates to thioureido-cyclodextrins, usable in particular to solubilize anti-tumor and antiparasitic agents and their preparation processes.

These thioureido-cyclodextrins correspond to the formula:

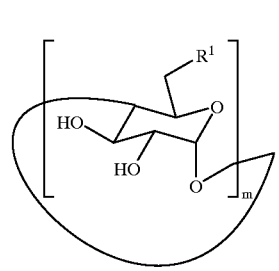

(I)

with m=6, 7 or 8, $R^1$ represents OH or NH—CS—NHR$^2$, at least one of the $R^1$ being NH—CS—NHR$^2$, $R^2$ represents an alkyl, monosaccharide, oligosaccharide glycosyl-amino acid or glycopeptide group.

These cyclodextrins are usable for solubilizing anti-tumor or antiparasitic agents of the Taxol family.

17 Claims, No Drawings

THIOUREIDO-CYCLODEXTRINS, UTILIZED IN PARTICULAR TO SOLUBILIZE ANTI-TUMOR, AND ANTIPARASITIC AGENTS AND THEIR PREPARATION PROCESSES

RELATED APPLICATIONS

This application is a 371 national stage application of PCT/FR97/00449, filed Mar. 13, 1997.

DESCRIPTION

The invention relates to thioureido-cyclodextrins, new derivatives of cyclodextrins, which can be utilized in particular to solubilize anti-tumor and antiparasitic agents in an aqueous medium, especially those of the Taxol family.

Cyclodextrins or cyclomalto-oligosaccharides, are cyclic oligosaccharides with the property of containing various molecules in their cavity, which are of a size adapted to the host structure. The generally nonpolar nature of these associations results in the preferential inclusion of hydrophobic structures that enable, in particular, the solubilization in water of compounds with little or no solubility in these media.

However, the relatively low solubility in water of cyclodextrins and, especially of β-cyclodextrin (18 g/l at 25° C.), the most economically accessible of them all, limits their use for this purpose.

To remedy this situation, the cyclodextrins were chemically modified to improve their solubility in water. The ramified derivatives of cyclodextrins consisting of one or more monosaccharide or oligosaccharide substituents linked to cyclodextrin by an atom of oxygen or sulfur as well as their uses were subsequently described in documents WO-A-95/19994, WO-A-95/21870 and EP-A-0 403 366. These ramified cyclodextrins are, in particular, likely to combine with Taxol and its derivatives, especially Taxotère®. These are anti-tumor and antiparasitic agents as described by P. Potier in Chem. Soc. Rev., 21, 1992, pp. 113–119, M. C. Bissery et al. in Cancer Research, 51, 1991, pp. 4845–4852 and J. Schrével et al. in Proc. Natl. Acad. Sci. USA, vol 91, pp. 8472–8476, 1994. Inclusion complexes are thus obtained, and these enable the anti-tumor agents to be solubilized in water. By way of example, the solubility in water of Taxotère®, which is 0.004 g/l, can be raised to 6.5 g/l by encapsulating it in 6'-S-α-maltosyl-6'-thiocyclomaltaheptaose, as has been described in WO-A-95/19994.

Document EP-A-0 605 753 describes Taxol inclusion complexes that use ramified cyclodextrins such as maltosyl-cyclodextrins, to increase the solubility in water of Taxol.

Cyclodextrin derivatives consisting of one or more glycosyl or maltosyl substituents linked to cyclodextrin by a sulfur atom are also described by V. Lainé et al. in J. Chem. Soc., Perkin Trans, 2, 1995, pp. 1479–1487. These derivatives have been tested to solubilize an active substance such as prednisolone.

The present invention relates to other cyclodextrin derivatives that do not only concern the solubilization of active substances, in particular anti-tumor and antiparasitic agents of the Taxol family, but also enable the targeting and vectoring of the active substance on organs to be treated.

The new cyclodextrin derivatives are thioureido-cyclodextrins that correspond to the formula:

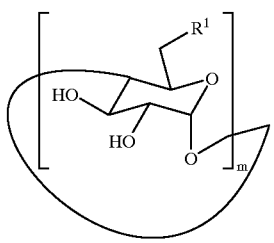

in which m is equal to 6, 7 or 8 and the R1s, which may be identical or different, represent OH or NH—CS—NHR$^2$ with R$^2$ representing an alkyl group, a group derived from a monosaccharide or an oligosaccharide that may be substituted if necessary, a glycosyl-amino acid derivative group, provided that at least one of the R$^1$ represents NH—CS—NHR$^2$ With these new derivatives, it is interesting to note the presence of a link or spacer of the —NH—CS—NH thiourea type instead of an oxygen or sulfur atom to bond the R$^2$ substituent. This occurs in particular when cyclodextrin is associated with a hydrophilic pattern such as a glucide derivative and is due to the simple nature of the coupling reaction. Furthermore, thioureas are very stable compounds with well-defined structures and can be coupled to a large number of substituents, as we will see further on. In fact, Thiourea-type compounds have been used in the preparation of neoglycoconjugates as has been described by Z. J. Witczak, Adv. Carbohyr. Chem., 44, 1986, pp. 91–145 and C. M. Reichert, C. E. Hayes and I. J. Goldstein, Methods Enzymol., 242, 1994, pp. 108–117.

Thiourea-cyclodextrins corresponding to formula (I) below may be cyclodextrins that are mono-substituted, per-substituted or partially substituted in primary alcohol position depending on the number of R$^1$ representing NH—CS—NHR$^2$. Moreover, the R$^2$ substituent(s) may be of various types.

Thus, R$^2$ may represent an alkyl group of one to ten carbon atoms, for example the methyl group. R$^2$ can also represent monosaccharide or oligosaccharide derivative groups that may be substituted if necessary. Examples of monosaccharide derivative groups are those groups derived from glucose and galactose, in a α or β form. Where the monosaccharide derivative group is substituted, one or more monosaccharide hydroxyl groups may be replaced by alcoxy groups with 1 to 16 carbon atoms, acyloxy groups such as the acetoxy group or by amine and amide groups. Derivative oligosaccharide groups may be maltosyl groups, maltotriosyl, lactosyl, or tri- or tetrasaccharide markers of cellular affinity of Lewis X or Sialyl Lewis X type, or oligosaccharides derived from heparin. They can also be substituted by alcoxy, acyloxy or amino groups.

According the invention, R$^2$ can also represent a group derived from a glycosyl amino acid or a glycopeptide.

The amino acids that are likely to be used are namely, natural amino acids such as alanine, cysteine, aspartic acid, glutamic acid, phenylalanine, glycine, histidine, isoleucine, lysine, leucine, methionine, asparagine, proline, glutamine, arginine, serine, threonine, valine, tryptophene and tyrosine. Modified amino acids may also be used.

In the case where the R$^2$ group contains a peptide, the group can be formed from the amino acids mentioned above. It can also contain modified amino acids.

The presence of an R$^2$ group of the glycosyl-amino acid or glycopeptide type gives cyclodextrin a special affinity for certain biological sites. This is because this group can act as an external molecular and cellular recognition marker. Thus, the modification of cyclodextrin enables the targeting and vectoring of an active substance contained in cyclodextrin.

The cyclodextrin derivatives in this invention can be prepared in two different ways. The first method (process A) consists in reacting an isothiocyanato-cyclodextrin with an amine containing the $R^2$ group. The second method (process B) consists in reacting an amino-cyclodextrin with a derivative containing an isothiocyanate function, itself containing the $R^2$ group.

The present invention therefore relates to an initial process (process A) for preparing a thioureido-cyclodextrin that corresponds to the formula (I) given below. The formula consists in reacting an isothiocyanate-cyclodextrin with the following formula:

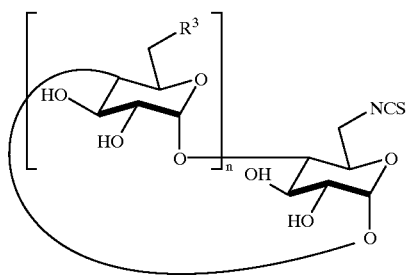

(II)

in which the $R^3$ of the isothiocyanate-cyclodextrin, which may be identical or different, represent NCS or OH and where n is equal to 5, 6 or 7 with an amine of a formula $R^2$—$NH_2$.

This reaction may be carried out in an organic solvent such as pyridine.

The isothiocyanate-cyclodextrin of formula (II) used as the starting product in this process may be prepared by the reaction of the corresponding amino-cyclodextrin with thiophosgene. For this preparation, we can use the process described by J. M. Garcia Fernandez et al. in Carbohydr. Res., 268, 1995, pp. 57–71.

The second process (process B) for preparing thiourea-cyclodextrins of formula (I) of the present invention consists in reacting an amino-cyclodextrin of formula:

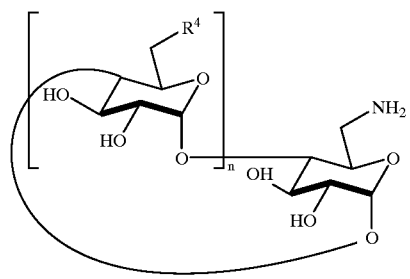

(III)

in which the $R^4$, which may be identical or different, represent OH or $NH_2$, and where n is equal to 5, 6 or 7, with an isothiocyanate of formula: $R^2$—NCS where $R^2$ has the signification given above, in the formula, the $R^4$, which may be identical or different, represent OH or $NH^2$, and n is equal to 5, 6 or 7, with an isothiocyanate of formula: $R^2$—NCS where $R^2$ has the signification given above.

This reaction may be carried out in an organic solvent such as pyridine.

The original amino-cyclodextrins of formula (III) can be prepared using the process described by J. M. Garcia Fernandez et al. in Carbohydr. Res., 268, 1995, pp. 57–71 mentioned above.

When $R^2$ is a group derived from a monosaccharide, an oligosaccharide, a glycosyl-amino acid or a glycopeptide, the isothiocyanate of formula $R^2$—NCS can be prepared by reacting thiophosgene with an aminodesoxyglycose or a glycosylamine.

In the case of process A, when the reactive agent is an amine of formula $R^2$—$NH_2$ where $R^2$ represents a group derived from a monosaccharide, an oligosaccharide, a glycosyl amino acid or a glycopeptide, the amine can be prepared by the process described by J. M. Garcia Fernandez et al. in J. Org. Chem, 58, 1993, pp. 5192–5199.

The processes described above that are used to obtain the thioureido-cyclodextrins of this invention are important because they make it possible to obtain the desired derivatives with a high output.

The thioureido-cyclodextrins in this invention can be utilized in particular to solubilize hydrophobic chemical compounds in an aqueous medium, especially anti-tumor agents that belong to the Taxol family.

Thus the invention also concerns the inclusion complexes of thioureido-cyclodextrins of formula (I) with a chemical compound, in particular hydrophobic ones such as a pharmaceutically active molecule.

In these inclusion complexes, the preferred chemical compound is an anti-tumor or antiparasitic agent, especially of the Taxol family such as Taxol or Taxotère®.

These inclusion complexes can be prepared using traditional processes. An example is the addition of the chemical compound in solution or in an undiluted form to a solution or suspension of the thioureido-cyclodextrin of formula (I) used.

In the case where a solution of the compound is added (an anti-tumor agent of the Taxol family, for example), a concentrated solution of the compound in an organic solvent that is miscible with water (acetone for example) is used. The mixture obtained is shaken and bubbled with an inert gas such as nitrogen to eliminate the organic solvent.

In the case of compounds of the Taxol family such as Taxotère®, the undiluted product can also be dispersed in a sterile solution of thioureido-cyclodextrin that conforms to this invention.

The invention also relates to a pharmaceutical composition that includes an inclusion complex of a cyclodextrin derivative of formula (I) and a pharmacologically active molecule such as an anti-tumor or antiparasitic agent with a medium that is pharmacologically acceptable.

Examples of these pharmaceutical compositions, which can be administered orally or parenterally, are solutions, powders, suspensions, etc. and, in particular injectable solutions.

Other characteristics and advantages of the invention will become clearer after the examples given below have been read. It is understood that these are given as examples and are not restrictive.

These examples relate to thioureido-cyclodextrins corresponding to the formula below:

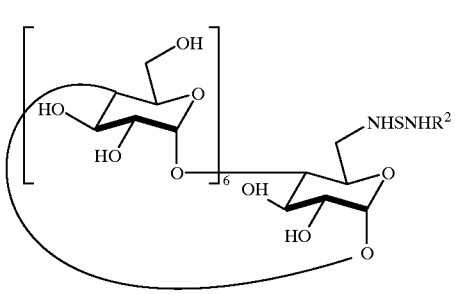

(IV)

EXAMPLE 1

Preparation of 6$^I$-desoxy-6$^I$-(N'-methylthioureido) cyclomaltoheptaose (compound n°1)

This compounds corresponds to formula (IV) given above in which R$^2$=CH$_3$.

It is obtained by condensing 6$^I$-amino-6$^I$-desoxycyclomaltoheptaose with methyl isothiocyanate (process B).

1. Preparation of 6$^I$-amino-6$^I$-desoxycyclomaltoheptaose 1,3-propanedithiol (0.62 ml, 6.15 mmol) and ethyldiisopropylamine (0.65 ml, 3.69 mmol) are added to a solution of 6$^I$-azido-6$^I$-desoxycyclomaltoheptaose (R. C. Petter, J. S. Salek, C. T. Sikorski, G. Kumaravel and F.-T Lin, J. Am. Chem. Soc., 112, 1990, pp. 3860–3868) in N,N-dimethylformamide (DMF, 10 ml). The reactional mixture is shaken at room temperature for 16 hours after which time acetone (100 ml) is added to it. The precipitate obtained is filtered, washed with acetone, redissolved in water (100 ml) and filtered over Celito. After the aqueous solution has been lyophilized, 1.34 g of amine (output 92%) is obtained. It corresponds to the $^{13}$C RMN described in the literature by S. E. Brown, J. H. Coates, D. R. Coghlan, C. J. Easton, S. J. van Eyk, W. Janowski, A. Lapore, S. F. Lincoln, Y. Luo, B. L. May, D. S. Scheisser, P. Wang and M. L. Williams, Aust. J. Chem., 46, 1993, pp. 953–958.

2. Preparation of compound n°1

Methyl isothiocyanate (8 mg, 0.1 mmol) is added to a solution of 6$^I$-amino-6$^I$-desoxycyclomaltoheptaose obtained in 1 (100 mg, 0.09 mmol) in pyridine (2 ml). The reactional mixture is kept at room temperature for 48 hours, and then concentrated. The residue obtained is dissolved in water (10 ml), shaken with chloroform (2×10 ml), the organic phase is decanted to separate the excess methyl isothiocyanate and the aqueous phase is lyophilized. 103 mg of compound n°1 (output 95%) with a purity of >90% (HPLC) is obtained. After the compound has been purified by HPLC (Nucleosil C-18, 5μ, Me-OH water eluent 12:88 v/v), compound n°1 (95 mg, 87%) is obtained. Its characteristics are shown below:

[α]$_D$+108.7° (c, 1.03, water);

mass spectrum (FAB$^+$): m/z 1229.2 (96%, [M+Na]$^+$), 1207.4 (100, [M+H]$^+$).

solubility in water: 775 g/l, 640 mM.

EXAMPLE 2

Preparation of 6$^I$-desoxy-6$^I$-[3-methyl-α-D-glucopyranosid-6-yl) thioureido)] cyclomaltoheptaose (compound n°2)

This compound corresponds to formula (IV) with R$^2$ corresponding to formula (V):

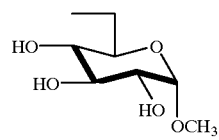

(V)

This compound is prepared by condensing 6$^I$-desoxy-6$^I$-isothiocyanatocyclomaltoheptaose with methyl 6-amino-6-desoxy-α-D-glucopyranoside (process A).

1. Preparation of 6$^I$-desoxy-6$^I$-isothiocyanatocyclomaltoheptaose

Calcium carbonate (0.9 g, 3 mmol) and thiophosgene (0.15 ml, 1.5 mmol) are added to a solution of 6$^I$-amino-6$^I$-desoxycyclomaltoheptaose (1.13 g, 1 mmol) in a water-acetone mixture (3:2, 75 ml). The suspension is shaken at room temperature for 16 hours and then concentrated to half its volume, diluted with water (30 ml) and demineralized by shaking it with the ion-exchange resin Amberlite MB-6113 (H+, OH; 5 ml) for 15 minutes. The aqueous solution is filtered and lyophilized. The characteristics of this product are show below:

[α]$_D$+112.1° (c 0.6, pyridine)

2. Preparation of methyl 6-amino-6-desoxy-α-D-glucopyranoside.

Methyl-6-amino-6-desoxy-α-D-glucopyranoside is prepared from commercial methyl-α-D-glucopyranoside in three stages. There is an overall output of 80% using the process described by J. M. Garcia Fernandez, C. Ortiz Mellet and J. Fuentes in J. Org. Chem., 58, 1993, pp. 5192–5199.

3. Preparation of compound 2.

Methyl 6-amino-6-desoxy-α-D-glucopyranoside obtained in 2 (16 mg, 85 μmol) is added to a solution of 6$^I$-desoxy-6$^I$-isothiocyanate-cyclomaltoheptaose obtained in phase 1 (100 mg, 85 μmol) in pyridine (3 ml). The reactional mixture is shaken at room temperature for 48 hours and then concentrated. Traces of pyridine are removed by co-evaporation with water (1 ml). The residue is then recovered by water and precipitated by adding ethanol. 110 mg of compound n°2 (output 95%) with a purity of >90% (HPLC) is obtained. After purification by HPLC (Nucleosil column, c-18, 5μ; Me-OH water eluent 12:88 v/v) compound n°2 is obtained. It has the following characteristics:

[α]$_D$+96.9° (c 0.66, water):

mass spectrum (FAB$^+$): m/z 1391.2 (20%, [M+Na$^+$], 1369.3 (100, [M+H]+), solubility in water: 710 g/l, 518 mM.

EXAMPLE 3

Preparation of 6$^I$-desoxy-6$^I$ [methyl-2,3,4-tri-O-acetyl α-D-glucopyranosid-6-yl)-thioureido) ]cyclomaltoheptaose (compound n°3)

This compound corresponds to formula (IV) with R$^2$ corresponding to formula (VI):

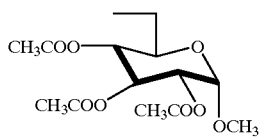

(VI)

It is prepared using process B.

Methyl 2,3,4-tri-0-acetyl-6-desoxy-6-isothiocyanate-α-D-glucopyranoside prepared according to the process by Garcia-Fernandez et al. In J. Org. Chem., 58, 1993 pp. 5192–5199—(36 mg, 0.1 mmol) is added to a solution of 6′-amino-6′-desoxycyclomaltoheptaose obtained in example 1 (118 mg, 0.1 mmol) in pyridine (2 ml). The reactional mixture is maintained at room temperature for 48 hours and then concentrated. The residue is dissolved in water (10 ml) washed with chloroform (2×10 ml) and lyophilized. 137 mg of compound n°3 (output of 92%) is obtained. The characteristics are shown below:

$[\alpha]_D$+116.1° (c 0.62, water)

mass spectrum (FAB+): m/z 1517.2 (100%, [M+Na]+), solubility in water: 558 g/l, 373 mM.

EXAMPLE 4 preparation of 6′-desoxy-6′-[3-N-glycyl-β-D-glucopyranosylamin-6-yl)thioureido)]cyclomaltoheptaose (compound n°4)

This compound corresponds to formula (IV) with $R^2$ corresponding to the formula:

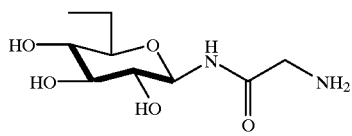

(VII)

The compound is obtained by the condensation of 6′-desoxy-6′-isothiocyanatocyclomaltoheptaose (see example 2) with the 6-amino-N-(N'tert-butyloxycarbonyl)glycyl-6-desoxy-β-D-glucopyranosylamine followed by the acidic hydrolysis of the tert-butyloxycarbonyl protecting group (process A).

1. Preparation of 6-amino-N(N'-tert-butyloxycarbonyl)glycyl-6-desoxy-β-D-glucopyranosylamine.

This compound is prepared in the following stages:

a) Preparation of 6-azido-6-desoxy-β-D-glucopyranosylamine.

Ammonium bicarbonate (1.92 g, 24.3 mmol) is added to a solution of 6-azido-6-desoxy-D-glucose (4.3 g, 24.3 mmol) —K. Dax et al., J. Carbohydr. Chem., 9, 1990, pp. 479–499—in aqueous ammonium hydroxide (16 M, 125 ml). The mixture is shaken at 40° C. for 30 hours and then concentrated to half its volume, diluted with water (150 ml) and lyophilized. The product obtained (4.3 g, 93%) contains 6-azido-6-desoxy-β-D-glucopyranosylamine with a purity of >80% ($^{13}$C RMN) that is utilized in the next stage without further purification.

b) Preparation of 6-azido-N-(N'-tert-butyloxycarbonyl)glycyl-6-desoxy-β-D-glucopyranosylamine.

Three solutions are added one after the other to a solution of N-(tert-butyloxycarbonyl)-glycine (66 mg, 0.40 mmol) in N,N-dimethylformamide (DMF, 1 ml). They are a solution of 6-azido-6-desoxy-β-D-glucopyranosylamine obtained in a) (100 mg, 0.49 mmol) in DMF (1 ml), a solution of 0-benzotriazol-1-yl-N,N,N'N'-tetramethyluronium hexafluorophosphate (HBTU, 0.55 g, 1.47 mmol) in DMF (5 ml), diisopropylethylamine (60 mg), and a solution of 1-hydroxybenzotriazole (HOBt, 66 mg, 0.49 mol) in DMF (1 ml). The mixture is shaken at room temperature for 16 hours, and then concentrated. The residue is purified by silica gel column chromatography (chloroform-methanol 19:1 v/v). 90 mg of 6-azido-N-(N'-tert-butyloxycarbonyl)glycyl-6-desoxy-β-D-glucopyranosylamine are obtained (55% output). The characteristics are shown below:

$[\alpha]_D$+3.8° (c 1.1 methanol)

c) Preparation of 6-amino-N-(N'-tert-butyloxycarbonyl)glycyl-6-desoxy-β-D-glucopyranosylamine 1,3-propanedithiol (0.19 ml, 1.87 mmol) and ethyldiisopropylamine (0.19 ml, 1.17 mmol) are added to a solution of 6-azido-N-(N'-tert-butyloxycarbonyl)glycyl-6-desoxy-β-D-glucopyranosylamine obtained in b) (0.14 g, 0.37 mmol) in DMF (6 ml). The reactional mixture is maintained at room temperature for three days and then concentrated. The residue is crystallized in ethanol-water. 125 mg of amine (output 92%) are obtained. The characteristics are shown below:

$[\alpha]_D$–5° (c, 0.08, water)

2. Preparation of 6′-desoxy-6′-{3'-[N-(N'-tert-butyloxycarbonyl) glycyl-β-D-glucopyranosylamino-6-yl]thioureido}cyclomaltoheptaose 6-amino-N-(N'-tert-butyl-oxycarbonyl)glycyl-6-desoxy-β-D-glucopyranosylamine (30 mg, 0.09 mol) is added to a solution of 6′-desoxy-6′-isothiocyanato-cyclomaltoheptaose (105 mg, 0.09 mmol) in pyridine (2 ml). The reactional mixture is maintained at room temperature for 3 days and then concentrated. Traces of pyridine are removed by co-evaporation with water. The residue is passed through water (1 ml) and precipitated by adding ethanol. 95 mg (70% output) of a white powder are obtained. The characteristics are shown below:

$[\alpha]_D$+103.4° (c 0.9, water);

mass spectrum (FAB+): m/z 1511.2 (100%, [M+H]+)

3. Preparation of compound n°4

A solution of 6′-desoxy-6′-{3'-[N-(N'-tert-butyloxycarbonyl) glycyl-β-D-glucopyranosylamine-6-yl]thioureido}cyclomaltoheptaose (77 mg, 51 μmol) in trifluoracetic acid-water (9:1 v/v, 1 ml) is maintained at room temperature for 1 hour and then concentrated. Traces of trifluoracetic acid are removed by co-evaporation with water. The residue is dissolved in water (5 ml), and the resultant solution is treated by the ion-exchange resin Amberlite IR-904 (OH−, 2 ml), filtered and lyophilized. 66 mg of compound n°4 (91% output) with a purity of > 95% (CLHP) is obtained. After purification by HPLC, compound n°4 (58 mg, 80%), comprising the characteristics below, is obtained:

$[\alpha]_D$+82.2° (c 1.8, water);

mass spectrum (FAB+): m/z 1411.3 (100%, M+H]+)

solubility in water: >800 g/l, 567 mM

EXAMPLE 5

Inclusion of Taxotère in 6′-desoxy-6′-(N'-methylthioureido)cyclomaltoheptaose (compound n°1)

The process is started with pure Taxotère and 2.1 mg (2.6 μmol) of the product in 3 ml of a solution containing 64.2 mmol/l of compound n°1 is dispersed in sterile water. The suspension obtained is shaken at room temperature until a clear solution is obtained. This indicates the encapsulation of Taxotère in the molecule of cyclodextrin. A significant increase of the solubility of Taxotère is obtained (4.7 g/l, 5.8 mmol/l). The solubility without cyclodextrin is 0.004 g/l.

What is claimed is:

1. Thioureido-cyclodextrin corresponding to the formula:

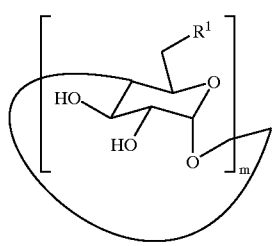

(I)

in which m is equal to 6, 7 or 8 and where the $R^1$, which may be identical or different, represent OH or NH—CS—NHR$^2$ with $R^2$ representing an alkyl group, a substituted or unsubstituted monosaccharide group or a substituted or unsubstituted oligosaccharide group, a glycosyl-amino acid group or a glycopeptide group, provided that at least one of the $R^1$ represents NH—CS—NHR$^2$.

2. Thioureido-cyclodextrin according to claim 1, wherein all $R^1$ represent —NH—CS—NH—R$^2$.

3. Thioureido-cyclodextrin according to claim 1, wherein one $R^1$ group represents —NH—CS—NHR$^2$ and the remaining $R^1$ groups are OH.

4. Thioureido-cyclodextrin according to claim 3, wherein $R^2$ is a methyl group.

5. Thioureido-cyclodextrin according to claim 2, wherein $R^2$ is a methyl-α-D-glucopyranosid-6-yle group.

6. Thioureido-cyclodextrin according to claim 3, wherein $R^2$ is a methyl-2,3,4-tri-0-acetyl-α-D-glucopyranosid-6-yle group.

7. Thioureido-cyclodextrin according to claim 3, wherein $R^2$ is a N-glycyl-β-D-glucopyranosylamin-6-yle group.

8. Preparation process of thioureido-cyclodextrin corresponding to the formula:

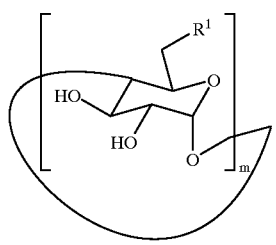

(I)

in which m is equal to 6, 7 or 8 and where the $R^1$, which may be identical or different, represent OH or NH—CS—NHR$^2$ with $R^2$ representing an alkyl group, a substituted or unsubstituted monosaccharide group or a substituted or unsubstituted oligosaccharide group, a glycosyl-amino acid group or a glycopeptide group, provided that at least one of the $R^1$ represents NH—CS—NHR$^2$, comprising reacting an isocyanato cyclodextrin of formula:

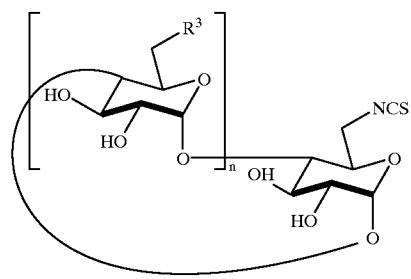

(II)

in which the $R^3$, which may be identical or different, represent OH or NCS, and where n is equal to 5, 6 or 7, with an amine of formula $R^2$—NH$_2$.

9. Preparation process of thioureido-cyclodextrin of formula:

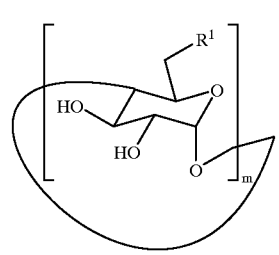

(I)

in which m is equal to 6, 7 or 8 and where the $R^1$, which may be identical or different represent OH or NH—CS—NHR$^2$ where $R^2$ represents an alkyl group, a substituted or unsubstituted monosaccharide group or a substituted or unsubstituted oligosaccharide group, a glycosyl-amino acid group or a glycopeptide group, provided that at least one of the $R^1$ represents NH—CS—NHR$^2$, comprising reacting an amino-cyclodextrin of formula:

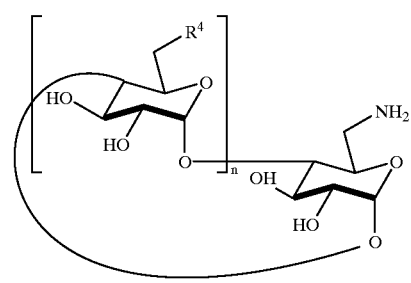

(III)

in which the $R^4$, which may be identical or different, represent OH or NH2, and where n is equal to 5, 6 or 7, with an isothiocyanate of formula $R^2$—NCS.

10. An inclusion complex of a thioureido-cyclodextrin represented by the formula:

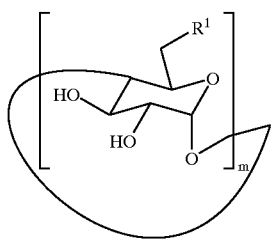 (I)

wherein m is equal to 6, 7 or 8;

each $R^1$, independently, represents OH or NH—CS—NHR$^2$, wherein $R^2$ represents an alkyl group, a substituted or unsubstituted monosaccharide group or a substituted or unsubstituted oligosaccharide group, a glycosyl-amino acid group or a glycopeptide group, provided at least one $R^1$ represents NH—CS—NHR$^2$, with a pharmaceutically active molecule.

11. A complex according to claim 10, wherein the pharmacologically active molecule is an anti-tumor or antiparasitic agent.

12. A complex according to claim 11, wherein the anti-tumor or antiparasitic agent belongs to the Taxol family.

13. A pharmaceutical composition comprising an inclusion complex of a thioureido-cyclodextrin according to claim 10, with a pharmacologically accepted vector.

14. A pharmaceutical composition according to claim 13, in the form of an aqueous solution.

15. A pharmaceutical composition according to claim 13, wherein the pharmacologically active molecule is an anti-tumor or antiparasitic agent.

16. A pharmaceutical composition according to claim 15, wherein the anti-tumor or antiparasitic agent belongs to the Taxol family.

17. A pharmaceutical composition according to claim 16, wherein one of the $R^1$ represents NHCSNHR$^2$, the other $R^1$ represent OH, $R^2$ is a methyl group, and m is equal to 7.

* * * * *